United States Patent
Wan et al.

(10) Patent No.: US 9,296,755 B2
(45) Date of Patent: Mar. 29, 2016

(54) 3,4-DIHYDRO-1H-PYRIMIDO[1,6-A]PYRIMIDIN-6(2H)-ONE COMPOUNDS AND THEIR THERAPEUTIC APPLICATIONS

(71) Applicant: GlaxoSmithKline Intellectual Property Development Limited, Brentford, Middlesex (GB)

(72) Inventors: Zehong Wan, Shanghai (CN); Xiaomin Zhang, Shanghai (CN)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/761,634

(22) PCT Filed: Jan. 23, 2014

(86) PCT No.: PCT/CN2014/071205
§ 371 (c)(1),
(2) Date: Jul. 17, 2015

(87) PCT Pub. No.: WO2014/114248
PCT Pub. Date: Jul. 31, 2014

(65) Prior Publication Data
US 2015/0322075 A1    Nov. 12, 2015

(30) Foreign Application Priority Data
Jan. 25, 2013  (WO) .............. PCT/CN2013/070970

(51) Int. Cl.
*C07D 487/04* (2006.01)

(52) U.S. Cl.
CPC ................................ *C07D 487/04* (2013.01)

(58) Field of Classification Search
None
See application file for complete search history.

(56) References Cited

U.S. PATENT DOCUMENTS

2008/0279846 A1  11/2008  Shi
2009/0246198 A1  10/2009  Dong et al.

FOREIGN PATENT DOCUMENTS

| WO | WO93/17682 | 9/1993 |
| WO | WO03/041712 | 5/2003 |
| WO | WO2004/031145 | 4/2004 |
| WO | WO 2004/031161 | 4/2004 |
| WO | WO 2008/048867 | 4/2008 |
| WO | WO 2011/072275 | 6/2011 |
| WO | WO 2013/014185 | 1/2013 |

OTHER PUBLICATIONS

Chemical Abstract Registry No. 859132-15-3, indexed in the Registry File on STN CAS Online Aug. 9, 2005.*

* cited by examiner

*Primary Examiner* — Rebecca Anderson
*Assistant Examiner* — Po-Chih Chen
(74) *Attorney, Agent, or Firm* — Fang Qian; William R. Majarian

(57) ABSTRACT

The present invention relates to novel 3,4-dihydro-1H-pyrimido[1,6-a]pyrimidin-6(2H)-one compounds that inhibit Lp-PLA$_2$ activity, processes for their preparation, to compositions containing them and to their use in the treatment of diseases associated with the activity of Lp-PLA$_2$, for example atherosclerosis, Alzheimer's disease.

12 Claims, No Drawings

US 9,296,755 B2

3,4-DIHYDRO-1H-PYRIMIDO[1,6-A]PYRIMIDIN-6(2H)-ONE COMPOUNDS AND THEIR THERAPEUTIC APPLICATIONS

This application is a 371 of International Application No. PCT/CN2014/071205, filed 23 Jan. 2014, which claims priority to PCT/CN2013/070970 filed 25 Jan. 2013.

RELATED APPLICATION

The present application claims priority from PCT International Application No. PCT/CN2013/070970 filed on Jan. 25, 2013 at the State Intellectual Property Office of the People's Republic of China, the entire contents of which is incorporated herein by reference.

FIELD OF THE INVENTION

The present invention relates to novel 3,4-dihydro-1H-pyrimido[1,6-a]pyrimidin-6(2H)-one compounds, processes for their preparation, intermediates useful in their preparation, pharmaceutical compositions containing them, and their use in therapy for the treatment of diseases or conditions mediated by Lp-PLA$_2$.

BACKGROUND OF THE INVENTION

Lipoprotein-associated phospholipase A$_2$ (Lp-PLA$_2$) previously known as platelet-activating factor acetylhydrolase (PAF-AH), is a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules derived from the oxidation of LDL. (See e.g., Zalewski A, et al., Arterioscler. Thromb. Vasc. Biol., 25, 5, 923-31(2005)). Lp-PLA$_2$ hydrolyzes the sn-2 ester of the oxidized phosphatidylcholines to give lipid mediators, lyso-phosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See. for example, published patent application nos. WO96/13484, WO96/19451, WO97/02242, WO97/12963, WO97/21675, WO97/21676, WO 97/41098, WO97/41099, WO99/24420, WO00/10980, WO0/66566, WO0/66567, WO0/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, and WO08/048866.) Disclosed uses include treating disease that involves or is associated with endothelial dysfunction, disease that involves lipid oxidation in conjunction with Lp-PLA$_2$ activity (e.g., associated with the formation of lyso-phosphatidylcholine and oxidized free fatty acids), and disease that involves activated monocytes, macrophages or lymphocytes or which is associated with increased involvement of monocytes, macrophages or lymphocytes. Examples of diseases include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's Disease, various neuropsychiatric disease such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176; JP 200188847; and US Published Patent Application Nos. US 2008/0279846 A1, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core. (See e.g., Wilensky et al., Current Opinion in Lipidology, 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., Nature Medicine, 10, 1015-1016 (2008)). These research results provided further evidence that Lp-PLA$_2$ inhibitors may be used to treat atherosclerosis.

Additional studies indicate that high Lp-PLA$_2$ activity is associated with high risk of dementia, including Alzheimer's disease (AD) (See e.g., Van Oijen, et al. Annals of Neurology, 59,139 (2006)). Higher levels of oxidized LDL have also been observed in AD patients (See e.g., Kassner et al. Current Alzheimer Research, 5, 358-366 (2008); Dildar, et al., Alzheimer Dis Assoc Disord, 24, Apr.-Jun. 2010; Sinem, et al. Current Alzheimer Research, 7, 463-469 (2010)). Further, studies show that neuroinflammation is present in AD patients and multiple cytotoxic inflammatory cytokines are up-regulated in AD patients. (See e.g., Colangelo, et al., Journal of Neuroscience Research, 70, 462-473 (2002); Wyss-Coray, Nature Medicine, 12, Sep. 2006). Research has shown that LysoPC function is a pro-inflammatory factor inducing multiple cytotoxic inflammatory cytokine release (See Shi, et al. Atherosclerosis, 191, 54-62 (2007)). Therefore, these studies provide additional evidence that that the inhibitors of Lp-PLA$_2$ can be used to treat AD by inhibiting activity of Lp-PLA$_2$ and reducing lysoPC production.

In addition, use of an Lp-PLA$_2$ inhibitor in a diabetic and hypercholesterolemia swine model demonstrated that blood-brain-barrier leakage and brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, Acta Neuropathol, 120, 277-286 (2010)). As discussed above, Lp-PLA$_2$ inhibitors can reduce inflammation, for example, reducing multiple cytokine release by suppressing lysoPC production. (See e.g., Shi, et al. Atherosclerosis 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wilensky et al., Current Opinion in Lipidology, 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic ocular disease.

Glaucoma and age-related macular degeneration (AMD) are retina neurodegenerative diseases. Studies suggest that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to compounds of Formula (I) and pharmaceutically acceptable salts thereof,

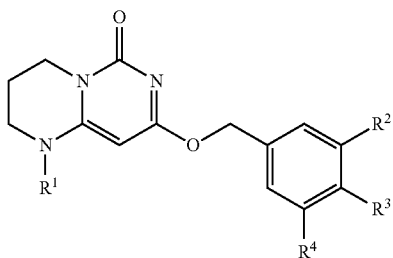

Formula (I)

wherein:
$R^1$ is selected from the group consisting of cyclopropyl, —CH$_2$—Ar and —CH$_2$—(C=O)—N(Ra)(Rb), wherein
  Ar is phenyl, optionally substituted with one or more substituents independently selected from the group consisting of halo, OCH$_3$, and CH$_3$, and
  Ra and Rb are each independently H or C$_{1-3}$alkyl,
  or Ra, Rb, together with the nitrogen atom to which they are attached, join together to form a nitrogen containing heterocyclic ring selected from the group consisting of pyrrolidinyl, morpholinyl, piperazinyl, and piperidinyl, wherein the nitrogen containing heterocyclic ring is optionally substituted with one or more substituents independently selected from the group consisting of C$_{1-3}$alkyl and halo;
$R^2$ is F or H,
$R^3$ is F or —O—Ar', wherein Ar' is phenyl substituted with one or more substituents independently selected from the group consisting of halo and CF$_3$, and
$R^4$ is selected from the group consisting of H, F and CN.

This invention also relates to a pharmaceutical composition comprising compounds of this invention and one or more pharmaceutically acceptable excipients.

The invention also relates to methods of treating or preventing a disease associated with the activity of Lp-PLA$_2$, which comprises administering to a subject in need thereof with a therapeutically effective amount of a compound of the invention described herein. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

This invention also provides methods of treating or preventing a disease by inhibiting Lp-PLA$_2$ activity. Exemplary diseases include, but are not limited to, neurodegeneration disease (e.g., Alzheimer's disease, vascular dementia), atherosclerosis, stroke, metabolic bone disorder (e.g., bone marrow abnormalities), dyslipidemia, Paget's diseases, type II diabetes, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD), psoriasis, and multiple sclerosis.

The methods comprise administering a therapeutically effective amount of a compound of this invention to a subject in need thereof. It is not intended that the present invention is limited to any particular stage of the disease (e.g. early or advanced).

This invention also provides methods of treating or preventing Alzheimer's disease. The methods comprise administering to a subject in need thereof a therapeutically effective amount of a compound of this invention.

This invention also provides methods of treating or preventing atherosclerosis. The methods comprise administering to a subject in need thereof a therapeutically effective amount of a compound of this invention.

This invention also provides methods of decreasing beta amyloid (also referred to as "Aβ") accumulation in the brain of a subject. The methods comprise administering to a subject in need thereof a therapeutically effective amount of a compound of the present invention. In certain embodiment, the beta amyloid is Abeta-42.

This invention also provides methods for treating or preventing ocular diseases by administering a compound of this invention. In certain embodiment, this invention provides methods of treating macular edema, which comprises administering to the subject a therapeutically effective amount of a compound of this invention. In certain embodiment, the macular edema is associated with diabetic ocular disease, for example, diabetic macular edema or diabetic retinopathy. In one embodiment, the macular edema is associated with posterior uveitis.

This invention also provides a use of compounds of this invention in the manufacture of a medicament for treating or preventing diseases described herein.

This invention also provides compounds of this invention for use in the treatment or prevention described herein.

DETAILED DESCRIPTION OF THE INVENTION

As used in the description of the embodiments of the invention and the appended claims, the singular forms "a", "an" and "the" are intended to include the plural forms as well, unless the context clearly indicates otherwise. Also, as used herein, "and/or" refers to encompasses any and all possible combinations of one or more of the associated listed items. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. Definitions

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

The term "neurodegeneration disease" as used herein refers to a varied assortment of central nervous system disorder characterized by gradual and progressive loss of neural tissue and/or neural tissue function. A neurodegeneration disease is a class of neurological disease where the neurological disease is characterized by a gradual and progressive loss of neural tissue, and/or altered neurological function, typically reduced neurological function as a result of a gradual and progressive loss of neural tissue. In certain embodiments, the neurodegeneration diseases described herein include neurodegeneration diseases where there is a defective blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

The term "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyrus), vascular dementia due to hemorrhagic lesions, small vessel disease (including, e.g. vascular dementia due to lacunar lesions and Binswanger disease), and mixed dementia.

The phrase "blood-brain barrier" or "BBB" are used interchangeably herein, and are used to refer to the permeable barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

The phrase "metabolic bone disease" as used herein refers to a varied assortment of bone diseases characterized by gradual and progressive loss of bone tissue. Metabolic bone diseases described herein are metabolic bone diseases where there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteiod synthesis.

The term "osteoporosis" refers to conditions in which mineral and/or bone matrix are decreased and/or bone mass is reduced.

"Alkyl" refers to a monovalent, saturated hydrocarbon chain having a specified number of carbon atoms. For example, $C_{1-3}$ alkyl refers to an alkyl group having from 1 to 3 carbon atoms. Alkyl groups may be straight or branched. In some embodiments, branched alkyl groups may have one, two, or three branches. Exemplary alkyl groups include, but are not limited to, methyl, methylethyl, ethyl, propyl (n-propyl and isopropyl), butyl (n-butyl, isobutyl, and t-butyl).

"Halogen" refers to fluorine (F), chlorine (Cl), bromine (Br), or iodine (I). "Halo" refers to the halogen radicals: fluoro (—F), chloro (—Cl), bromo (—Br), or iodo (—I).

"Optionally substituted" indicates that a group, such as phenyl, or nitrogen containing heterocyclic ring (e.g., pyrrolidinyl, morpholinyl, piperazinyl, or piperidinyl), may be unsubstituted, or the group may be substituted with one or more substituents as defined.

"Nitrogen containing heterocyclic ring" refers to a 5 or 6-membered saturated monoheterocyclic ring which contains at least one nitrogen atom. Optionally, the ring may contain one additional heteroatoms selected from oxygen or nitrogen. Examples of nitrogen containing heterocyclic rings include pyrrolidinyl, morpholinyl, piperazinyl, or piperidinyl.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, halo, $OCH_3$, $C_{1-3}$alkyl, and $CF_3$. Suitable substituents are defined herein for each substituted or optionally substituted group.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and particularly human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, the term "therapeutically effective amount" means any amount which, as compared to a corresponding subject who has not received such amount, results in treating or preventing a disease, but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, compounds of Formula I and pharmaceutically acceptable salts thereof:

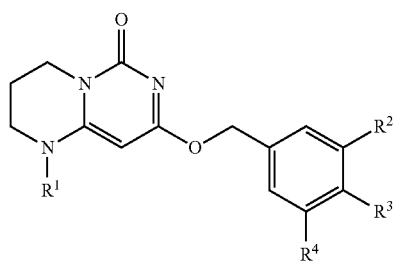

Formula (I)

wherein:

$R^1$ is selected from the group consisting of cyclopropyl, —$CH_2$—Ar and —$CH_2$—(C=O)—N(Ra)(Rb), wherein Ar is phenyl, optionally substituted with one or more substituents independently selected from the group consisting of halo, $OCH_3$, and $CH_3$, and Ra and Rb are each independently H or $C_{1-3}$alkyl, or Ra, Rb, together with the nitrogen atom to which they are attached, join together to form a nitrogen containing heterocyclic ring selected from the group consisting of pyrrolidinyl, morpholinyl, piperazinyl and piperidinyl, wherein the nitrogen containing heterocyclic ring is optionally substituted with one or more substituents independently selected from the group consisting of $C_{1-3}$alkyl and halo;

$R^2$ is F or H, $R^3$ is F or —O—Ar', wherein Ar' is phenyl substituted with one or more substituents independently selected from the group consisting of halo and $CF_3$, and $R^4$ is selected from the group consisting of H, F and CN.

In one embodiment, this invention relates to compounds of Formula (I), wherein $R^1$ is —$CH_2$—(C=O)—N(Ra)(Rb), wherein Ra, Rb, together with the nitrogen atom to which they are attached, join together to form a nitrogen containing heterocyclic ring selected from the group consisting of morpholinyl, piperazinyl, and piperidinyl, wherein the nitrogen containing heterocyclic ring is optionally substituted with one or two substituents independently selected from the group consisting of F and $CH_3$, or pharmaceutically acceptable salts thereof. In one embodiment, this invention relates to compounds of Formula (I), wherein $R^1$ is —$CH_2$—Ar, wherein Ar is phenyl, optionally substituted with one or two substituents independently selected from the group consisting of F, Cl, $OCH_3$, and $CH_3$, or pharmaceutically acceptable salts thereof. In yet a further embodiment, this invention relates to compounds of Formula (I), wherein $R^1$ is cyclopropyl or pharmaceutically acceptable salts thereof.

In another embodiment, this invention relates to compounds of Formula (I) and any of the above applicable embodiments, wherein $R^2$ is H or pharmaceutically acceptable salts thereof. In another embodiment, this invention relates to compounds of Formula (I) and any of the above applicable embodiments, wherein $R^2$ is F or pharmaceutically acceptable salts thereof.

In one embodiment, this invention relates to compounds of Formula (I) and any of the above applicable embodiments, wherein $R^3$ is F or pharmaceutically acceptable salts thereof.

Further, in one embodiment, this invention also relates to compounds of Formula (I) and any of the above applicable embodiments, wherein $R^3$ is —O—Ar', wherein Ar' is phenyl substituted with one or two substituents independently selected from the group consisting of halo and $CF_3$ or pharmaceutically acceptable salts thereof.

In one embodiment, this invention relates to compounds of Formula (I) and any of the above applicable embodiments, wherein $R^4$ is H or F pharmaceutically acceptable salts thereof. In one embodiment, this invention also relates to compounds of Formula (I) and any of the above applicable embodiments, wherein $R^4$ is F or pharmaceutically acceptable salts thereof.

In one embodiment, this invention relates to a compound has the structure of

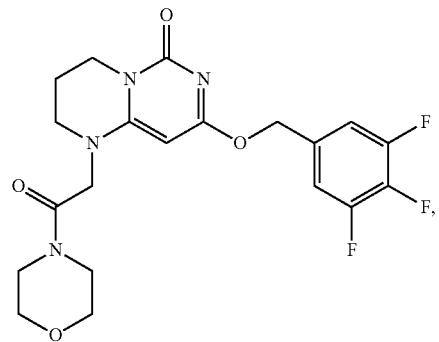

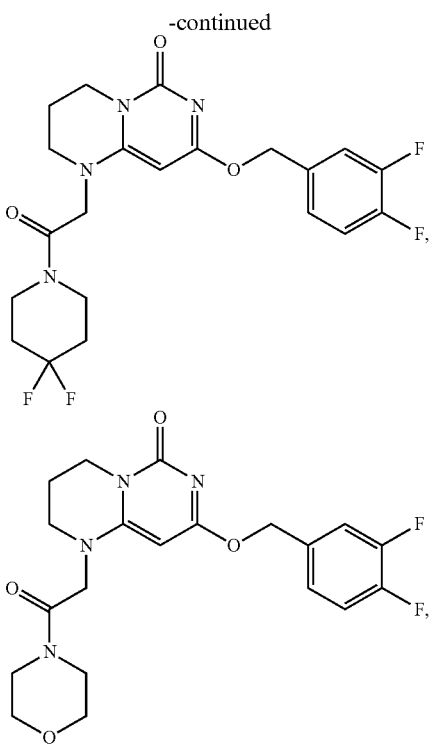

or a pharmaceutically acceptable salt thereof.

In one embodiment, the compound of Formula (I) is a compound of any one of Examples 1 to 24, a free base form, a free acid form, or a salt (e.g., a pharmaceutically acceptable salt) thereof.

The compounds of Formula (I), salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), salts (e.g., pharmaceutically acceptable salts) thereof as mixtures with isomers thereof in which one or more chiral centers are inverted. Likewise, it is understood that the compounds of Formula (I), salts (e.g., pharmaceutically acceptable salts) thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I), salts (e.g., pharmaceutically acceptable salts) thereof, as well as any wholly or partially equilibrated mixtures thereof. The present invention also includes the individual isomers of the compounds of Formula (I), salts (e.g., pharmaceutically acceptable salts) thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods, or any given isomer may be obtained by conventional synthetic methods or by stereospecific or asymmetric syntheses.

The invention also includes various deuterated forms of compounds of Formula (I), salts (e.g., pharmaceutically acceptable salts) thereof. Each available hydrogen atom attached to a carbon atom may be independently replaced with a deuterium atom. A person of ordinary skill in the art will know how to synthesize deuterated forms of compounds of Formula (I), salts (e.g., pharmaceutically acceptable salts) thereof. Commercially available deuterated starting materials may be employed in the preparation of deuterated forms of compounds of Formula (I), salts (e.g., pharmaceutically acceptable salts) thereof, or they may be synthesized using conventional techniques employing deuterated reagents (e.g. lithium aluminum deuteride).

In addition to the free base or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

The compounds described herein, their salts (e.g., pharmaceutically acceptable salts), deuterated form, solvates or hydrates thereof, may exist in one or more polymorphic form.

Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

The compounds of Formula (I) and salts (including pharmaceutically acceptable salts) thereof may be in the form of a solvate. For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethylsulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Solvates include stoichiometric solvates as well as compositions containing variable amounts of the incorporated solvent(s), e.g. a hydrate includes stoichiometic hydrates and compositions containing variable amounts of water.

The invention also includes isotopically-labeled compounds and salts, which are identical to compounds of Formula (I) or salts thereof, but for the fact that one or more atoms are replaced by an atom having an atomic mass or mass number different from the atomic mass or mass number most commonly found in nature. Examples of isotopes that can be incorporated into compounds of Formula (I) or salts thereof isotopes of hydrogen, carbon, nitrogen, fluorine, such as $^3$H, $^{11}$C, $^{14}$C and $^{18}$F. Such isotopically-labeled compound of Formula (I) or salts thereof are useful in drug and/or substrate tissue distribution assays. For example, $^{11}$C and $^{18}$F isotopes are useful in PET (positron emission tomography). PET is useful in brain imaging. Isotopically-labeled compounds of Formula (I) and salts thereof can generally be prepared by carrying out the procedures disclosed below, by substituting a readily available isotopically-labeled reagent for a non-isotopically labeled reagent. In one embodiment, compounds of Formula (I) or salts thereof are not isotopically labeled.

As used herein, the terms "compound(s) of the invention" or "compound(s) of the present invention" mean a compound of Formula (I), as defined herein, in any form, i.e., any salt or non-salt form (e.g., as a free acid or base form, or as a salt, for example, a pharmaceutically acceptable salt thereof), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, a compound of the invention includes a compound of Formula (I), or a salt thereof, for example a pharmaceutically acceptable salt thereof. Representative compounds of this invention include the specific compounds described.

C. Synthesis of Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below. All starting material and reagents described in the below general experimental schemes are commercially available.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Experimental Scheme 1

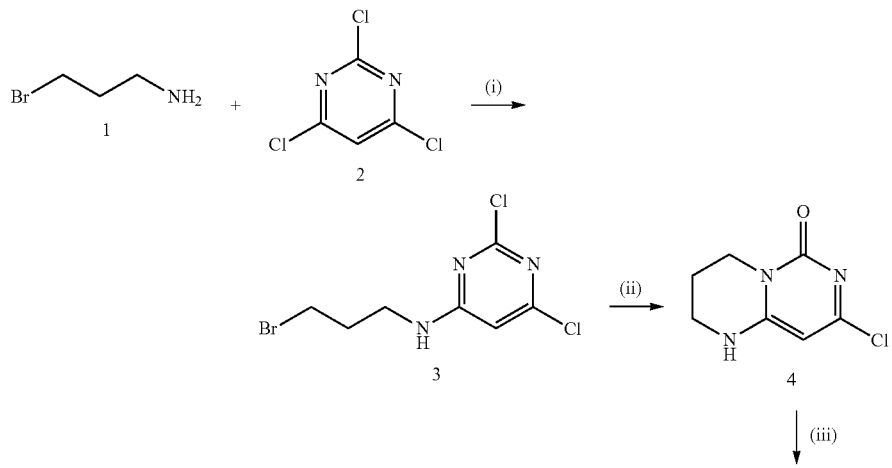

-continued

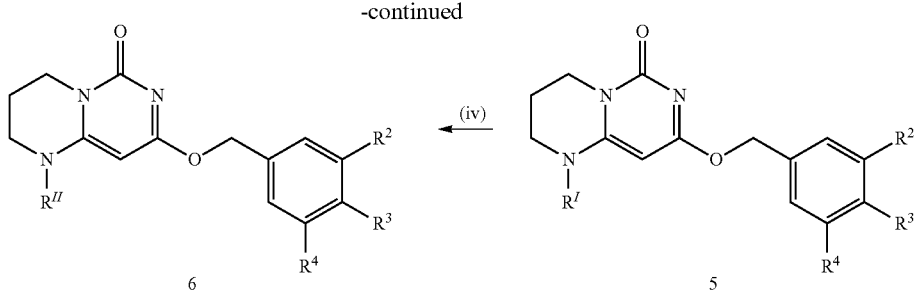

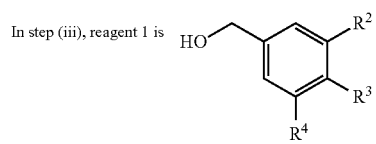

In step (iii), reagent 1 is $R^I$ is —CH$_2$COOH or —CH$_2$—Ar, Ar is defined in Formula (I)
$R^{II}$ is —CH$_2$-(C=O)-B(Ra)(Rb) and Ra, Rb are as defined in Formula (I)
$R^2$, $R^3$, $R^4$, Ar, Ra an Rb are as defined in Formula (I)

General Experimental Scheme 1 provides an exemplary synthesis for compounds 5 and 6. Step (i) may be carried out by reacting compound 1 with compound 2 using an appropriate base such as triethylamine in an appropriate solvent such as acetonitrile under room temperature to provide compound 3.

Step (ii) may be carried out by hydrolysis and followed up with alkylation reaction using an appropriate base such as potassium carbonate in an appropriate solvent such as a mixture of dioxane at a suitable temperature such as 60° C. and water to provide compound 4.

Step (iii) may be divided into two steps. The first step may be carried out by reacting compound 4 with bromo acetic acid or halo-(CH$_2$)—Ar in the presence of a suitable base such as NaH in a suitable solvent such as dimethylformamide (DMF) at a suitable temperature such as 50° C. or room temperature. The second step may be carried out by continuing to react with reagent 1 in the presence of a suitable base such as NaH in a suitable solvent such as dimethylformamide (DMF) at a suitable temperature such as room temperature to provide compound 5.

When $R^1$ is —CH$_2$COOH, compound 5 may continue to carry out in step (iv) by reacting with an appropriate amine in the presence of a suitable base such as Hunig's base and HATU in a suitable solvent such as tetrahydofuran (THF) at room temperature to provide compound 6.

General Experimental Scheme 2

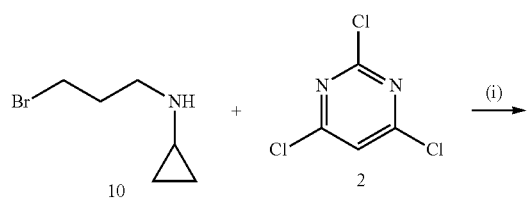

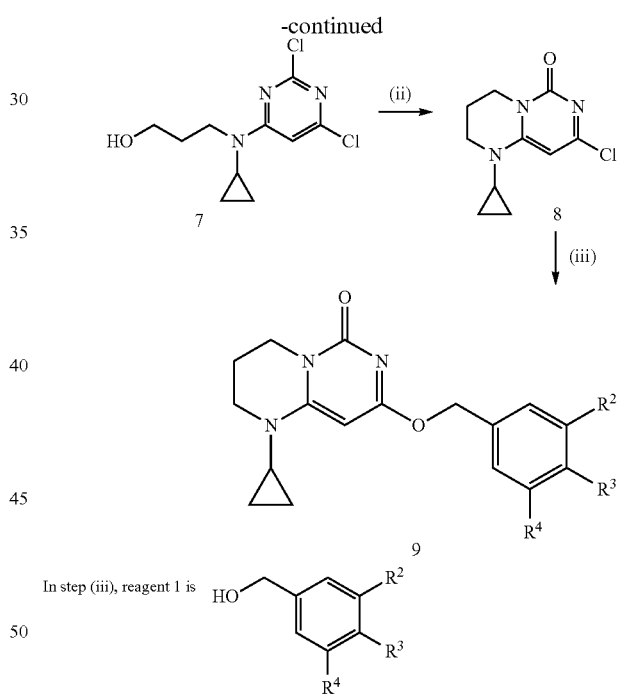

In step (iii), reagent 1 is

General Experimental Scheme 2 provides an exemplary synthesis for compounds 9. Step (i) may be carried out by reacting compound 10 with compound 2 using an appropriate base such as triethylamine in an appropriate solvent such as acetonitrile at room temperature to provide compound 7.

Step (ii) may be carried out by hydrolysis followed up with intra-molecular Mitsunobu reaction using appropriate reagents such as diisopropyl azodicarboxylate (DIAD) and Ph$_3$P in a suitable solvent such as THF at a suitable temperature such as room temperature to provide compound 8.

Step (iii) may be taken place using reagent 1 in the presence of a suitable base such as NaH in a suitable solvent such as dimethylformamide (DMF) at suitable temperature such as room temperature to provide compound 9.

All temperatures are reported in degrees Celsius. All other abbreviations are as described in the ACS Style Guide (American Chemical Society, Washington, D.C., 1986).

LCMS Conditions:

1) Acidic Conditions:

Mobile phase: water containing 0.05% TFA/0.05% acetonitrile

Column: Agilent SB-C18 4.6×30 mm-1.8 microns

Detection: MS and photodiode array detector (PDA)

2) Basic Conditions:

Mobile phase: water containing 10 mmol NH$_4$HCO$_3$/acetonitrile

Column: XBridge™ C18 4.6×50 mm-3.5 microns

Detection: MS and photodiode array detector (PDA)

Mass Directed Autoprep Purification (MDAP) Conditions:

1) Acidic Conditions:

Instrument: Waters instrument

Column: Sunfire Prep C18 column (5 um, 19×50 mm)

Mobile phase: water containing 0.05% TFA/acetonitrile.

2) Basic Conditions:

Instrument: Waters instrument

Column: Xbridge Prep C18 column (5 um, 19×50 mm)

Mobile phase: water containing 0.04% ammonia/acetonitrile.

Abbreviations and Resource Sources

The following abbreviations and resources are used herein below:

ISCO system—Teledyne ISCO (http://www.isco.com/html/seFlashChromatography.html)

r.t/rt/RT—room temperature

ACN—acetonitrile

Aq.—aqueous

CV—Column volumes

DCM—dichloromethane

DIAD—diisopropyl azodiformate

DMF—dimethylformamide

DMSO—dimethyl sulfoxide

EA—ethyl acetate

FC—flash chromatography

HATU—2-(1H-7-Azabenzotriazol-1-yl)-1,1,3,3-tetramethyl uronium hexafluorophosphate methanaminium TEA—triethylamine TFA—trifluoro acetic acid THF—tetrahydrofuran PE—petroleum ether

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

D1

N-(3-bromopropyl)-2,6-dichloropyrimidin-4-amine

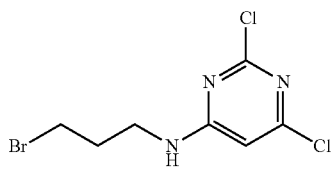 [SMILES: Clc1cc(NCCCBr)nc(Cl)n1]

To a solution of 2,4,6-trichloropyrimidine (10 g, 54.5 mmol) in acetonitrile (200 mL) was added triethylamine (22.80 mL, 164 mmol) at 0° C., stirred for 5 min at r.t., and then added dropwise a solution of 3-bromopropan-1-amine hydrochloride (12 g, 68.8 mmol) in N,N-dimethylformamide (5 mL). The reaction mixture was stirred for 1 h at r.t., filtered, and concentrated. Purification via FC afforded the title compound (5.6 g).

LC-MS (ESI): m/z 285 [M+1]$^+$; 3.01 (ret time).

D2

8-chloro-3,4-dihydro-1H-pyrimido[1,6-a]pyrimidin-6(2H)-one

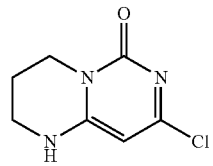 [SMILES: O=c1nc(Cl)cc2n1CCCN2]

To a solution of N-(3-bromopropyl)-2,6-dichloropyrimidin-4-amine (2.0 g, 7.02 mmol) in 1,4-dioxane (15 mL) and water (15 mL) was added potassium carbonate (2.0 g, 14.47 mmol), stirred for 2 h at 60° C. and then concentrated. The residue was neutralized to pH~6 by hydrochloride solution (6M), extracted by ethyl acetate to remove byproduct, and then neutralized by sodium hyroxide (2M) to pH~7. The water was removed in vacuum to afford the title compound (3.03 g).

LC-MS (ESI): m/z 186 [M+1]$^+$; 0.40 (ret time).

D3

1-benzyl-8-chloro-3,4-dihydro-1H-pyrimido[1,6-a]pyrimidin-6(2H)-one

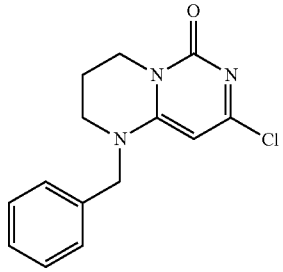 [SMILES: O=c1nc(Cl)cc2n1CCCN2Cc1ccccc1]

To a suspension of 8-chloro-3,4-dihydro-1H-pyrimido[1,6-a]pyrimidin-6(2H)-one (1 g, 2.32 mmol) and sodium hydride (0.28 g, 6.95 mmol) in N,N-dimethylformamide (10 mL) was added (bromomethyl)benzene (0.40 mL, 2.78 mmol) at room temperature, and stirred for 30 min at r.t. Purification via reverse phase column (0.3% TFA in water/acetonitrile) afforded the title compound (300 mg).

LC-MS (ESI): m/z 276 [M+1]$^+$; 1.98 (ret time).

D4

3-(cyclopropylamino) propan-1-ol

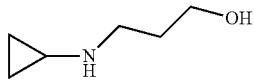

To a solution of cyclopropanamine (5 g, 88 mmol) in ethanol (120 mL), was added 3-bromopropan-1-ol (6.09 g, 43.8 mmol), refluxed for 14 h, and concentrated to afford the title compound for next step without further purification.

D5

3-(cyclopropyl(2,6-dichloropyrimidin-4-yl)amino) propan-1-ol

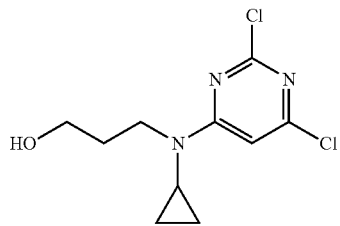 [SMILES: OCCCN(c1cc(Cl)nc(Cl)n1)C1CC1]

To a solution of 3-(cyclopropylamino)propan-1-ol (7 g, 60.8 mmol) and Hunig's base (31.8 mL, 182 mmol) in N,N-dimethylformamide (20 mL), was added 2,4,6-trichloropyrimidine (7.10 mL, 60.8 mmol), stirred for 3 h at 0° C. Then, EtOAc (150 mL) was added, and the organic phase was washed with water, brine, dried over Na$_2$SO$_4$, and concentrated. Purification via FC afforded the title compound (3.8 g).

LC-MS (ESI): m/z 263 [M+1]$^+$; 2.65 min (ret time).

D6

4-chloro-6-(cyclopropyl(3-hydroxypropyl)amino) pyrimidin-2(1H)-one

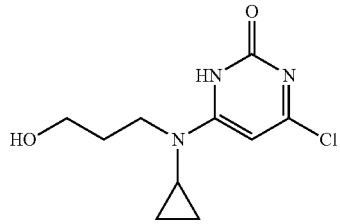 [SMILES: O=c1nc(Cl)cc(N(CCCO)C2CC2)[nH]1]

To a solution of 3-(cyclopropyl(2,6-dichloropyrimidin-4-yl)amino)propan-1-ol (5.0 g, 19.07 mmol) in 1,4-dioxane (50 mL) was added a solution of NaOH (7.63 g, 191 mmol) in water (50 mL) at r.t, stirred for 4 h at 100° C. The organic solvent was removed under reduce vacuum and the PH was adjusted to 8 with aq. HCl (12 N). Purification via reverse C-18 column afforded the title compound (2.1 g) as a white solid.

LC-MS (ESI): m/z 244 [M+1]$^+$; 1.36 min (ret time).

D7

8-chloro-1-cyclopropyl-3,4-dihydro-1H-pyrimido[1,6-a]pyrimidin-6(2H)-one

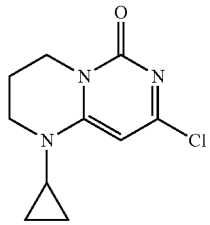 [SMILES: O=c1nc(Cl)cc2n1CCCN2C1CC1]

To a solution of 4-chloro-6-(cyclopropyl(3-hydroxypropyl)amino) pyrimidin-2(1H)-one (2 g, 8.21 mmol) in tetrahydrofuran (20 mL) were added DIAD (2.394 mL, 12.31 mmol) and triphenylphosphine (3.23 g, 12.31 mmol) at r.t., stirred for 3 h, and concentrated. Purification via C-18 column, and afforded the title compound as a white solid.

LC-MS (ESI): m/z 226 [M+1]$^+$; 1.37 min (ret time).

D8

2-(8-((3,4-difluorobenzyl)oxy)-6-oxo-2,3,4,6-tetrahydro-1H-pyrimido[1,6-a]pyrimidin-1-yl)acetic acid

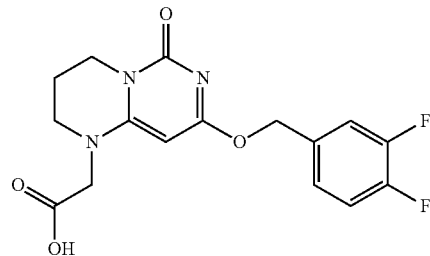 [SMILES: O=C(O)CN1CCCn2c1cc(OCc1ccc(F)c(F)c1)nc2=O]

To a solution of 8-chloro-3,4-dihydro-1H-pyrimido[1,6-a]pyrimidin-6(2H)-one (5 g, 26.9 mmol) in tetrahydrofuran (20 mL) was added sodium hydride (2.59 g, 108 mmol) at r.t. stirred for 10 minutes at r.t., then was added ethyl 2-bromoacetate (4.50 g, 26.9 mmol) and stirred for 2 h, and followed by addition of (3,4-difluoro phenyl)methanol (3.88 g, 26.9 mmol). The reaction mixture was stirred for 1 h at r.t., quenched by addition of water, and extracted by EtOAc. The aqueous phase was acidified to pH~1 with HCl (1N), washed by EtOAc, then the aqueous phase was concentrated in vacuum, and the residual was washed by methanol and filtrated. The filtrate was concentrated to afford the title compound (3.1 g)

LC-MS (ESI): m/z 352 [M+1]$^+$; 0.78 (ret time).

D9

2-(6-oxo-8-((3,4,5-trifluorobenzyl)oxy)-2,3,4,6-tetrahydro-1H-pyrimido[1,6-a]pyrimidin-1-yl)acetic acid

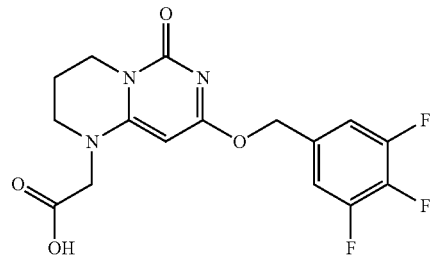 [SMILES: O=C(O)CN1CCCn2c1cc(OCc1cc(F)c(F)c(F)c1)nc2=O]

The title compound was prepared by a procedure similar to that described for D8 starting from 8-chloro-3,4-dihydro-1H-pyrimido[1,6-a]pyrimidin-6(2H)-one.

LC-MS (ESI): m/z 370 [M+1]⁺: 2.60 min (ret time)

Examples

E1

1-benzyl-8-((3,4-difluorobenzyl)oxy)-3,4-dihydro-1H-pyrimido[1,6-a]pyrimidin-6(2H)-one

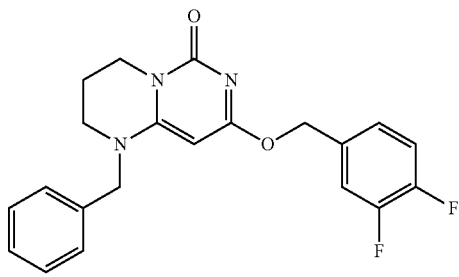 [SMILES: O=c1nc(OCc2ccc(F)c(F)c2)cc2n1CCCN2Cc1ccccc1]

To a suspension of NaH (21.76 mg, 0.54 mmol) in N,N-dimethylformamide (DMF) (2 mL), 1-benzyl-8-chloro-3,4-dihydro-1H-pyrimido[1,6-a]pyrimidin-6(2H)-one (50 mg, 0.18 mmol) was added (3,4-difluorophenyl)methanol (0.026 mL, 0.22 mmol) at r.t., and stirred for 30 mins. The reaction mixture was quenched by water. Purification via reverse phase column (0.3% trifluoroacetate acid in acetonitrile/water) afforded the title compound (22 mg).

LC-MS (ESI): m/z 384 [M+1]⁺; 2.54 (ret time).

E2

1-(4-chlorobenzyl)-8-((3,4-difluorobenzyl)oxy)-3,4-dihydro-1H-pyrimido[1,6-a]pyrimidin-6(2H)-one

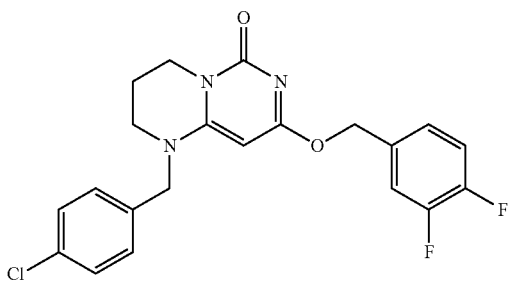 [SMILES: O=c1nc(OCc2ccc(F)c(F)c2)cc2n1CCCN2Cc1ccc(Cl)cc1]

To a solution of 8-chloro-3,4-dihydro-1H-pyrimido[1,6-a]pyrimidin-6(2H)-one (50 mg, 0.27 mmol) and sodium hydride (23.70 mg, 0.59 mmol) in anhydrous N,N-dimethylformamide (3 mL) was added a solution of 1-(bromomethyl)-4-chlorobenzene (66.4 mg, 0.32 mmol) in anhydrous N,N-dimethylformamide (1 ml) at r.t, and then stirred for 1 h at 50° C. Then, a solution of (3,4-difluorophenyl) methanol (46.6 mg, 0.32 mmol) in N,N-dimethylformamide (1 ml) was added and stirred for 1 h at r.t. The reaction mixture was quenched by water. Purification via reverse phase column using acetonitrile/water as eluent afforded the title compound (13 mg).

LC-MS (ESI): m/z 418 [M+1]⁺: 2.74 min (ret time)

E4

8-((3,4-difluorobenzyl)oxy)-1-(4-fluorobenzyl)-3,4-dihydro-1H-pyrimido[1,6-a]pyrimidin-6(2H)-one

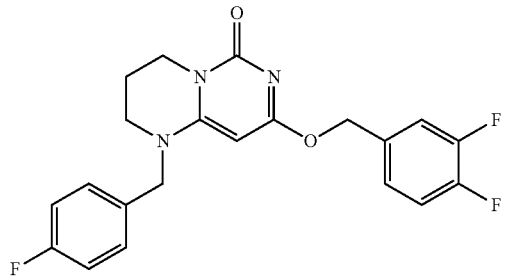 [SMILES: O=c1nc(OCc2ccc(F)c(F)c2)cc2n1CCCN2Cc1ccc(F)cc1]

The title compound was prepared by a procedure similar to that described for E2 starting from 8-chloro-3,4-dihydro-1H-pyrimido[1,6-a]pyrimidin-6(2H)-one, 1-(bromomethyl)-4-fluorobenzene and (3,4-difluorophenyl)methanol.

LC-MS (ESI): m/z 402 [M+1]⁺: 2.58 min (ret time)

E4

8-((3,4-difluorobenzyl)oxy)-1-(4-methoxybenzyl)-3,4-dihydro-1H-pyrimido[1,6-a]pyrimidin-6(2H)-one

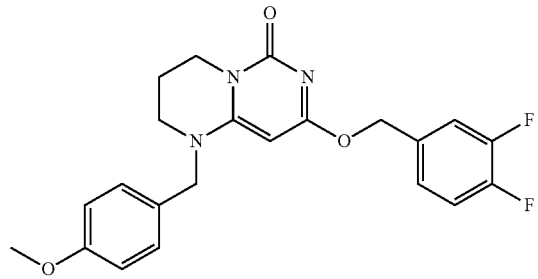 [SMILES: COc1ccc(CN2CCCn3c2cc(OCc2ccc(F)c(F)c2)nc3=O)cc1]

The title compound was prepared by a procedure similar to that described for E2 starting from 8-chloro-1-methyl-3,4-dihydro-1H-pyrimido[1,6-a]pyrimidin-6(2H)-one, 1-(bromomethyl)-4-methoxybenzene and (3,4-difluorophenyl)methanol.

LC-MS (ESI): m/z 414 [M+1]+; 2.56 (ret time).

E5

1-(3,4-difluorobenzyl)-8-((3,4-difluorobenzyl)oxy)-3,4-dihydro-1H-pyrimido[1,6-a]pyrimidin-6(2H)-one

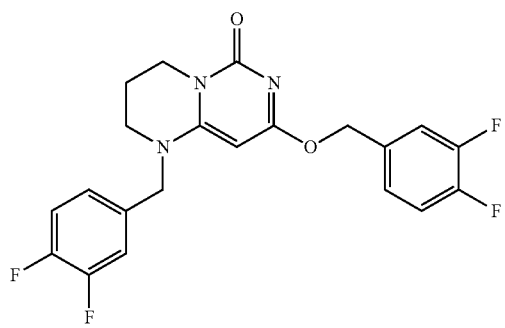 [SMILES: O=c1nc(OCc2ccc(F)c(F)c2)cc2n1CCCN2Cc1ccc(F)c(F)c1]

The title compound was prepared by a procedure similar to that described for E2 starting from 8-chloro-1-methyl-3,4-dihydro-1H-pyrimido[1,6-a]pyrimidin-6(2H)-one, 4-(bromomethyl)-1,2-difluorobenzene and (3,4-difluorophenyl)methanol.

LC-MS (ESI): m/z 420 [M+1]$^+$; 2.63 (ret time).

E6

8-((3,4-difluorobenzyl)oxy)-1-(3-methoxybenzyl)-3,4-dihydro-1H-pyrimido[1,6-a]pyrimidin-6(2H)-one

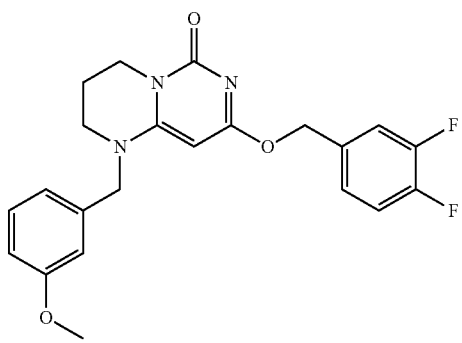 [SMILES: COc1cccc(CN2CCCn3c2cc(OCc2ccc(F)c(F)c2)nc3=O)c1]

The title compound was prepared by a procedure similar to that described for E2 starting from 8-chloro-1-methyl-3,4-dihydro-1H-pyrimido[1,6-a]pyrimidin-6(2H)-one, 1-(bromomethyl)-3-methoxybenzene and (3,4-difluorophenyl)methanol.

LC-MS (ESI): m/z 414 [M+1]+; 2.56 (ret time).

E7

8-((3,4-difluorobenzyl)oxy)-1-(2-methylbenzyl)-3,4-dihydro-1H-pyrimdo[1,6-a]pyrimidin-6(2H)-one

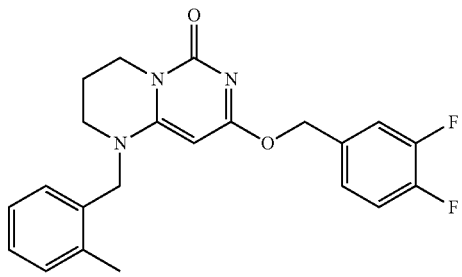 [SMILES: Cc1ccccc1CN1CCCn2c1cc(OCc1ccc(F)c(F)c1)nc2=O]

The title compound was prepared by a procedure similar to that described for E2 starting from 8-chloro-1-methyl-3,4-dihydro-1H-pyrimido[1,6-a]pyrimidin-6(2H)-one and 1-(bromomethyl)-2-methylbenzene and (3,4-difluorophenyl)methanol.

LC-MS (ESI): m/z 398 [M+1]$^+$; 2.71 (ret time).

E8

8-((4-(4-chloro-3-(trifluoromethyl)phenoxy)-3-fluorobenzyl)oxy)-1-cyclopropyl-3,4-dihydro-1H-pyrimido[1,6-a]pyrimidin-6(2H)-one

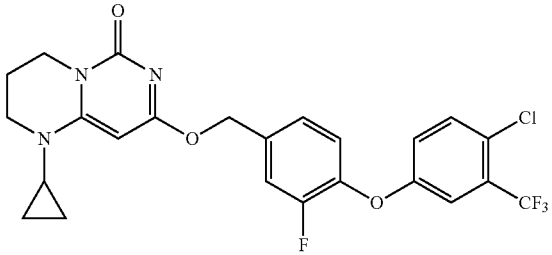 [SMILES: O=c1nc(OCc2ccc(Oc3ccc(Cl)c(C(F)(F)F)c3)c(F)c2)cc2n1CCCN2C1CC1]

The title compound was prepared by a procedure similar to that described for E2 starting from 8-chloro-1-cyclopropyl-3,4-dihydro-1H-pyrimido[1,6-a]pyrimidin-6(2H)-one and (4-(4-chloro-3-(trifluoromethyl)phenoxy)-3-fluorophenyl)methanol.

LC-MS (ESI): m/z 510 [M+1]$^+$; 3.12 min (ret time).

E9

1-cyclopropyl-8-((3-fluoro-4-(3-(trifluoromethyl)phenoxy)benzyl)oxy)-3,4-dihydro-1H-pyrimido[1,6-a]pyrimidin-6(2H)-one

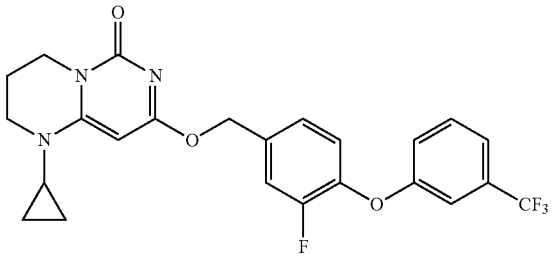 [SMILES: O=c1nc(OCc2ccc(Oc3cccc(C(F)(F)F)c3)c(F)c2)cc2n1CCCN2C1CC1]

The title compound was prepared by a procedure similar to that described for E2 starting from 8-chloro-1-cyclopropyl-3,4-dihydro-1H-pyrimido[1,6-a]pyrimidin-6(2H)-one and (3-fluoro-4-(3-(trifluoromethyl)phenoxy)phenyl) methanol.

LC-MS (ESI): m/z 476 [M+1]$^+$; 3.03 min (ret time).

E10

1-cyclopropyl-8-((4-(3,4-difluorophenoxy)-3-fluorobenzyl)oxy)-3,4-dihydro-1H-pyrimido[1,6-a]pyrimidin-6(2H)-one

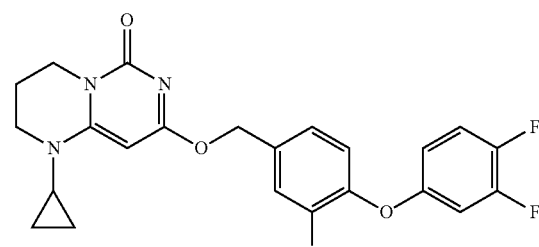

The title compound was prepared by a procedure similar to that described for E2 starting from 8-chloro-1-cyclopropyl-3,4-dihydro-1H-pyrimido[1,6-a]pyrimidin-6(2H)-one and (4-(3,4-difluorophenoxy)-3-fluorophenyl)methanol.

LC-MS (ESI): m/z 444 [M+1]⁺; 2.71 min (ret time).

E11

2-(4-chloro-3-(trifluoromethyl)phenoxy)-5-(((1-cyclopropyl-6-oxo-2,3,4,6-tetrahydro-1H-pyrimido[1,6-a]pyrimidin-8-yl)oxy)methyl)benzonitrile

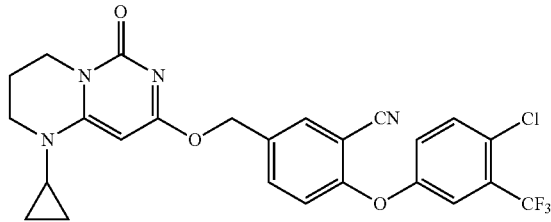 [SMILES: N#Cc1cc(COc2cc3n(c(=O)n2)CCCN3C2CC2)ccc1Oc1ccc(Cl)c(C(F)(F)F)c1]

The title compound was prepared by a procedure similar to that described for E2 starting from 8-chloro-1-cyclopropyl-3,4-dihydro-1H-pyrimido[1,6-a]pyrimidin-6(2H)-one and 2-(4-chloro-3-(trifluoromethyl) phenoxy)-5-(hydroxymethyl)benzonitrile.

LC-MS (ESI): m/z 517 [M+1]⁺; 2.98 min (ret time).

E12

1-cyclopropyl-8-((3-fluoro-4-(3-fluorophenoxy)benzyl)oxy)-3,4-dihydro-1H-pyrimido[1,6-a]pyrimidin-6(2H)-one

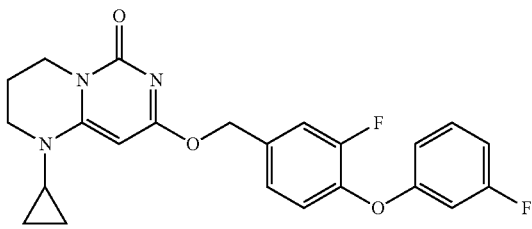 [SMILES: O=c1nc(OCc2ccc(Oc3cccc(F)c3)c(F)c2)cc2n1CCCN2C1CC1]

The title compound was prepared by a procedure similar to that described for E2 starting from 8-chloro-1-cyclopropyl-3,4-dihydro-1H-pyrimido[1,6-a]pyrimidin-6(2H)-one and (3-fluoro-4-(3-fluorophenoxy)phenyl) methanol.

LC-MS (ESI): m/z 426 [M+1]⁺; 2.62 min (ret time).

E13

2-(8-((3,4-difluorobenzyl)oxy)-6-oxo-2,3,4,6-tetrahydro-1H-pyrimido[1,6-a]pyrimidin-1-yl)-N-propylacetamide

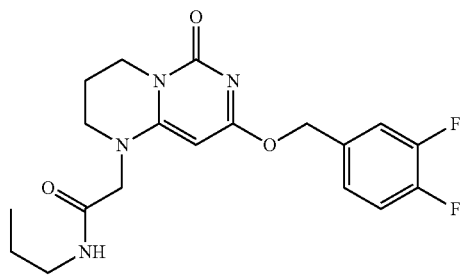 [SMILES: CCCNC(=O)CN1CCCn2c1cc(OCc1ccc(F)c(F)c1)nc2=O]

To a solution of 2-(8-((3,4-difluorobenzyl)oxy)-6-oxo-2,3,4,6-tetrahydro-1H-pyrimido[1,6-a]pyrimidin-1-yl)acetic acid (300 mg, 0.854 mmol), Hunig's base (0.597 mL, 3.42 mmol) and HATU (487 mg, 1.281 mmol) in tetrahydrofuran (10 mL) was added propan-1-amine (76 mg, 1.281 mmol). The reaction mixture was stirred at 20° C. for 2 hours. The solution was concentrated and purified by MDAP, to afford title compound (20 mg, 0.049 mmol, 5.69% yield).

LC-MS (ESI): m/z 393 [M+1]⁺; 0.78 (ret time).

E14

1-(2-oxo-2-(pyrrolidin-1-yl)ethyl)-8-((3,4,5-trifluorobenzyl)oxy)-3,4-dihydro-1H-pyrimido[1,6-a]pyrimidin-6(2H)-one

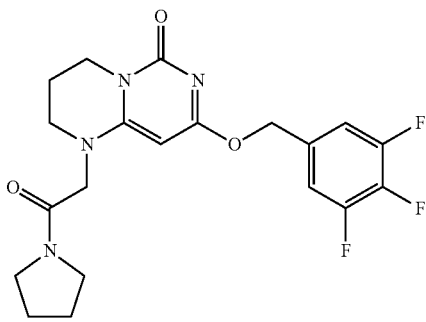 [SMILES: O=C(CN1CCCn2c1cc(OCc1cc(F)c(F)c(F)c1)nc2=O)N1CCCC1]

The title compound was prepared by a procedure similar to that described for E13 starting from 2-(6-oxo-8-((3,4,5-trifluorobenzyl)oxy)-2,3,4,6-tetrahydro-1H-pyrimido[1,6-a]pyrimidin-1-yl) acetic acid and pyrrolidine.

LC-MS (ESI): m/z 423 [M+1]⁺; 0.83 (ret time).

E15

N-methyl-2-(6-oxo-8-((3,4,5-trifluorobenzyl)oxy)-2,3,4,6-tetrahydro-H-pyrimido[1,6-a]pyrimidin-1-yl) acetamide

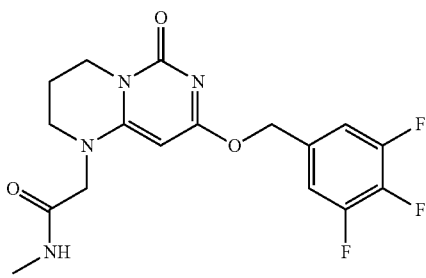 [SMILES: CNC(=O)CN1CCCn2c1cc(OCc1cc(F)c(F)c(F)c1)nc2=O]

The title compound was prepared by a procedure similar to that described for E13 starting from 2-(6-oxo-8-((3,4,5-trifluorobenzyl)oxy)-2,3,4,6-tetrahydro-1H-pyrimido[1,6-a]pyrimidin-1-yl) acetic acid and methanamine.

LC-MS (ESI): m/z 383 [M+1]⁺; 0.72 (ret time).

E16

1-(2-morpholino-2-oxoethyl)-8-((3,4,5-trifluorobenzyl)oxy)-3,4-dihydro-1H-pyrimido[1,6-a]pyrimidin-6(2H)-one

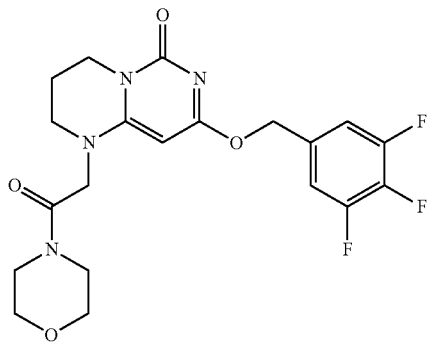 [SMILES: O=C(CN1CCCn2c1cc(OCc1cc(F)c(F)c(F)c1)nc2=O)N1CCOCC1]

The title compound was prepared by a procedure similar to that described for E13 starting from 2-(6-oxo-8-((3,4,5-trifluorobenzyl)oxy)-2,3,4,6-tetrahydro-1H-pyrimido[1,6-a]pyrimidin-1-yl) acetic acid and morpholine.
LC-MS (ESI): m/z 439 [M+1]$^+$; 0.76 (ret time)

E17

2-((3,4-difluorobenzyl)oxy)-6-oxo-2,3,4,6-tetrahydro-1H-pyrimido[1,6-a]pyrimidin-1-yl)-N-methylacetamide

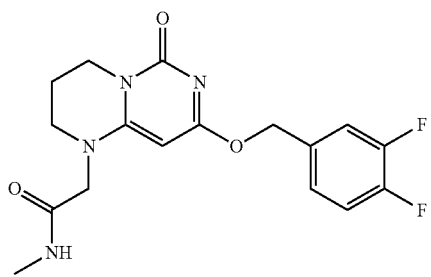 [SMILES: CNC(=O)CN1CCCn2c1cc(OCc1ccc(F)c(F)c1)nc2=O]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and methanamine.
LC-MS (ESI): m/z 365 [M+1]$^+$; 0.90 (ret time).

E18

8-((3,4-difluorobenzyl)oxy)-1-(2-oxo-2-(pyrrolidin-1-yl)ethyl)-3,4-dihydro-1H-pyrimido[1,6-a]pyrimidin-6(2H)-one

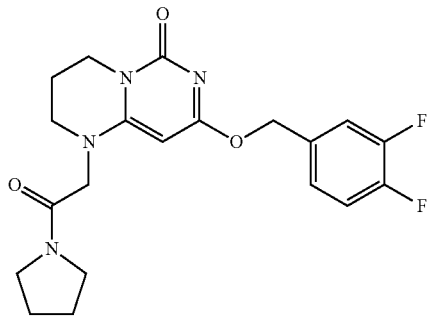 [SMILES: O=C(CN1CCCn2c1cc(OCc1ccc(F)c(F)c1)nc2=O)N1CCCC1]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and pyrrolidine.
LC-MS (ESI): m/z 405 [M+1]$^+$; 1.02 (ret time).

E19

8-((3,4-difluorobenzyl)oxy)-1-(2-(4-methylpiperazin-1-yl)-2-oxoethyl)-3,4-dihydro-1H-pyrimido[1,6-a]pyrimidin-6(2H)-one

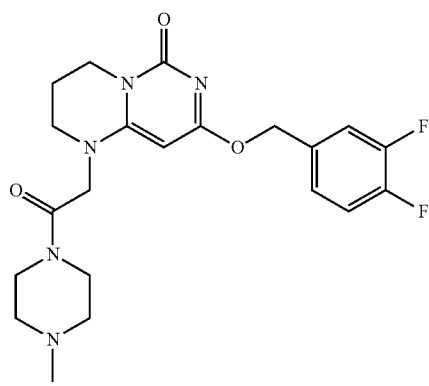 [SMILES: CN1CCN(C(=O)CN2CCCn3c2cc(OCc2ccc(F)c(F)c2)nc3=O)CC1]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and 1-methylpiperazine.
LC-MS (ESI): m/z 434 [M+1]*; 0.80 (ret time).

E20

8-((3,4-difluorobenzyl)oxy)-1-(2-(4,4-difluoropiperidin-1-yl)-2-oxoethyl)-3,4-dihydro-1H-pyrimido[1,6-a]pyrimidin-6(2H)-one

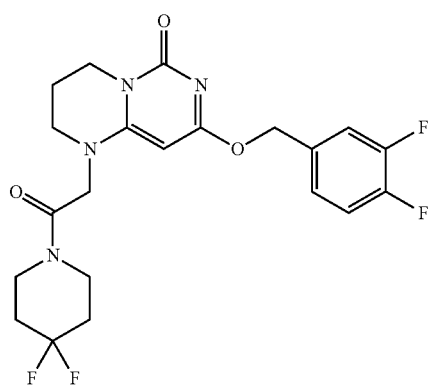 [SMILES: O=C(CN1CCCn2c1cc(OCc1ccc(F)c(F)c1)nc2=O)N1CCC(F)(F)CC1]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and 4,4-difluoropiperidine.
LC-MS (ESI): m/z 455 [M+1]$^+$; 1.10 (ret time).

E21

8-((3,4-difluorobenzyl)oxy)-1-(2-oxo-2-(piperidin-1-yl)ethyl)-3,4-dihydro-H-pyrimido[1,6-a]pyrimidin-6(2H)-one

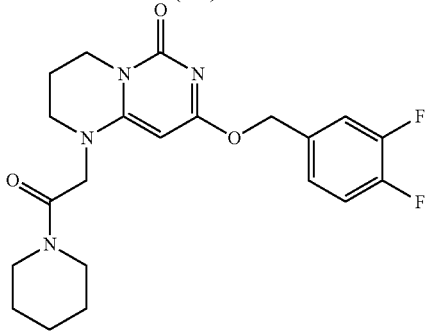 [SMILES: O=C(CN1CCCn2c1cc(OCc1ccc(F)c(F)c1)nc2=O)N1CCCCC1]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and piperidine.
LC-MS (ESI): m/z 419 [M+1]$^+$; 1.08 (ret time).

E22

8-((3,4-difluorobenzyl)oxy)-1-(2-morpholino-2-oxoethyl)-3,4-dihydro-H-pyrimido[1,6-a]pyrimidin-6(2H)-one

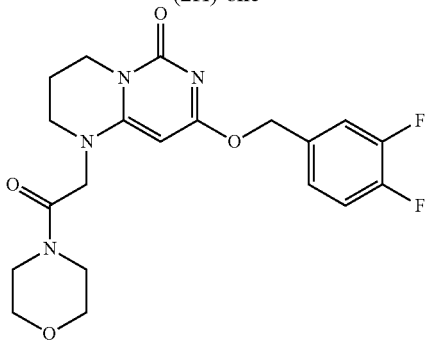

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and morpholine.
LC-MS (ESI): m/z 421 [M+1]$^+$; 0.93 (ret time).

E23

8-((3,4-difluorobenzyl)oxy)-1-(2-(4-fluoropiperidin-1-yl)-2-oxoethyl)-3,4-dihydro-1H-pyrimido[1,6-a]pyrimidin-6(2H)-one

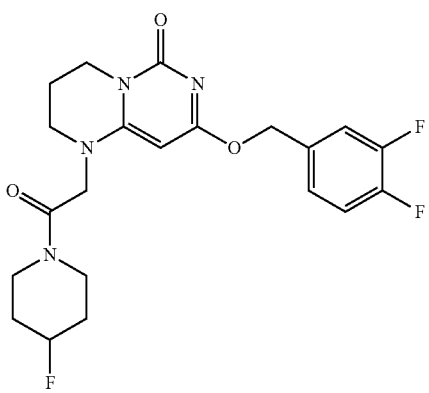 [SMILES: O=C(CN1CCCn2c1cc(OCc1ccc(F)c(F)c1)nc2=O)N1CCC(F)CC1]

The title compound was prepared by a procedure similar to that described for E13 starting from 2-(8-((3,4-difluorobenzyl)oxy)-6-oxo-2,3,4,6-tetrahydro-1H-pyrimido[1,6-a]pyrimidin-1-yl)acetic acid and 4-fluoropiperidine.
LC-MS (ESI): m/z 437 [M+1]$^+$; 1.06 (ret time).

E24

2-(6-oxo-8-((3,4,5-trifluorobenzyl)oxy)-2,3,4,6-tetrahydro-1H-pyrimido[1,6-a]pyrimidin-1-yl)-N-propylacetamide

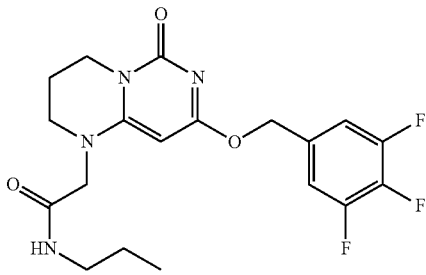 [SMILES: CCCNC(=O)CN1CCCn2c1cc(OCc1cc(F)c(F)c(F)c1)nc2=O]

The title compound was prepared by a procedure similar to that described for E13 starting from 2-(6-oxo-8-((3,4,5-trifluorobenzyl)oxy)-2,3,4,6-tetrahydro-1H-pyrimido[1,6-a] pyrimidin-1-yl) acetic acid and propan-1-amine.
LC-MS (ESI): m/z 411 [M+1]$^+$; 0.84 (ret time).

D. Biological Assays and Data

The compounds of present invention are Lp-PLA$_2$ inhibitors, and are useful in the treatment and prevention of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-Associated Phospholpase A2 (Lp-PLA$_2$) Biochemical Assay (1) Recombinant Human Lp-PLA$_2$ Assay (rhLp-PLA$_2$) (Also Referred to as "PED6" Assay)

N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Invitrogene and Molecular Probes. There is a quenching para-nitro phenyl (PNP) group in the sn3 position and a Bodipy fluorescein (FL) group in the sn2 position. Upon cleavage with Lp-PLA$_2$, the Bodipy FL group is liberated and then may result in an increase in fluorescence. Inhibitors of Lp-PLA$_2$ therefore prevent this cleavage and no fluorescent increase is observed.

The PED6 assay was run as an unquenched 10 μL assay. The source plate containing the compounds to be tested was prepared by making 1:3 (by volume) serial dilution of the compounds within DMSO on 384-well microplate. Then, 0.01 µL of the compounds on compound source plate were transferred into 384 well Greiner 784076 (black) plates using ECHO liquid dispenser. 5 µL of recombinant human Lp-PLA$_2$ enzyme (4 nM (or 110 pM) rhLp-PLA$_2$ in assay buffer of 50 mM HEPES, pH 7.4, 150 mM NaCl, 1 mM CHAPS) was added to each well of the plate. Plates were centrifuged for 10 sec at 500 rpm. After 30 minutes preincubation, 5 µL of substrate (4 µM (or 5 µM) PED6 [from 5 mM DMSO stock] in assay buffer of 50 mM HEPES, pH 7.4, 150 mM NaCl, 1 mM CHAPS) was added to 384 well Greiner 784076 (black) plates. Plates were centrifuged for 10 sec at 500 rpm. The plate was covered to protect it from light and incubated for 20 min at room temperature. The plates were read for fluorescence intensity at ex: 480/em: 540 using ViewLux microplate imager for Envision spectrofluroimeters. PIC50 data, curve and QC analysis was conducted by using XL fit module in Excel.

All compounds of Examples E1-E24 of the present invention were tested according to the of recombinant human Lp-PLA$_2$ assay described above and were found to demonstrate inhibition activity to Lp-PLA$_2$. The pIC$_{50}$ value for each compound was either reported in at least one experiment or the average of multiple experiments.

The pIC$_{50}$ values in the recombinant human Lp-PLA$_2$ assay for compounds of Examples E1-E24 were at least 8.0.

The pIC$_{50}$ values in the recombinant human Lp-PLA$_2$ assay for Examples E2, E4, E8, E11, E16, E19, E20, E22 and E23 were at least 9.0.

For example, the pIC50 values of recombinant human Lp-PLA$_2$ assay for following examples are:

| Example No. | rhLp-PLA$_2$ (PED6 assay) (pIC50) |
| --- | --- |
| E2 | 9.2 |
| E4 | 9.0 |
| E6 | 8.8 |
| E8 | 9.3 |
| E11 | 9.1 |
| E13 | 8.5 |
| E16 | 9.3 |
| E19 | 9.5 |
| E20 | 9.7 |
| E22 | 9.1 |
| E23 | 9.1 |

(2) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, PLA2 VIIB liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 µL assay. The source plate containing the compounds is prepared by making 1:3 (by volume) serial dilution of the compounds with pure DMSO on 384-well microplate. 0.01 µL of compounds on the compound source plate were transferred into 384 well Greiner 784076 (black) plates by ECHO liquid dispenser. 5 µL of Novel Serine Dependent Lipase (NSDL) enzyme (5 nM NSDL in assay buffer of 50 mM HEPES, pH 7.4, 150 mM NaCl, 1 mM CHAPS) was added to each well. Alternatively, in some instances, this step was carried out by adding 10 µL of recombinant human PLA2 VIIB (200 pM rhPLA$_2$ VIIB in assay buffer of 50 mM HEPES, pH 7.4, 150 mM NaCl, 1 mM CHAPS) to each well. Plates were centrifuged for 10 sec at 500 rpm. After 30 minutes preincubation, 5 µL of substrate (5 µM PED6 [from 5 mM DMSO stock] in assay buffer of 50 mM HEPES, pH 7.4, 150 mM NaCl, 1 mM CHAPS) was added to 384 well Greiner 784076 (black) low-volume plates. Plates were kinetic read by starting read immediately after PED6 addition at ex: 480/em:540 using ViewLux microplate reader or Envision spectrofluorimeters. IC 50 data (which may be converted to pIC50 data), curve and QC analysis was conducted using XLfit module in Excel.

The compounds of Examples E1-E24 of the present invention were tested in PLA2 VIIB assay as described above. All tested compounds except Example E7 had over 100 fold selectivity between human recombinant Lp-PLA$_2$ and PLA2 VIIB.

(3) Lipoprotein-Associated Phospholipase A2 (Lp-PLA$_2$) Human Plasma Assay (Also Referred to as "Thio-PAF Assay")

The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluoresence after Michael addition of thiols. This assay may detect the activity of Lp-PLA$_2$ in human plasma, as determined by specific inhibition by Lp-PLA$_2$ inhibitors.

The thio-PAF assay was run as a quenched 15 µL assay. Compounds source plate was prepared by making 1:3 (by volume) serial dilution of the compounds into pure DMSO on 384-well microplate. 0.01 µL of compounds on compound source plate were transferred to 384 well Greiner 784076 (black) low-volume plates by ECHO liquid dispenser. 8 µL pooled human plasma, which was previously aliquoted and frozen, was added. Plates were centrifuged for 10 sec at 500 rpm. After 30 minutes preincubation, 2 µL of substrate solution comprising 2.5 mM 2-thio-PAF [from ethanol stock], 32 µM CPM [from a DMSO stock] and 3.2 mM NEM (N-ethylmaleimide) [made fresh daily in DMSO] in assay buffer of 50 mM HEPES, pH 7.4, 150 mM NaCl, 1 mM CHAPS was added to 384 well Greiner 784076 (black) low-volume plates by BRAVO liquid handling station. After 2 mins, reaction was quenched with 5 µL of 5% aqueous trifluoroacetic acid (TFA). Plates were covered to protect from light and incubated for 40 min at room temperature. Plates were read at ex: 380/em: 485 using Envision microplate reader. PIC50 data, curve and QC analysis were conducted by using XLFit module in Excel.

The compounds of Examples E1-E24 of the present invention were tested in thio-PAF assay described above or similar assays.

The pIC$_{50}$ values in the thio-PAF assay for Examples E1-E24 were at least 6.0.

The pIC$_{50}$ values in the thio-PAF assay for Examples E1, E3, E4, E6, E8, E9, E11, E13, E14 and E16-E24 were at least 7.0.

E. Methods of Use

The compounds of the invention are inhibitors of Lp-PLA$_2$. Therefore, these compounds may be used in therapy, for example, in the treatment or prevention of diseases associated with the activity of Lp-PLA$_2$, which comprises treating a subject in need thereof with a therapeutically effective amount of an inhibitor of Lp-PLA$_2$. Accordingly, one aspect of the invention is directed to methods of treating or preventing diseases associated with the activity of Lp-PLA$_2$. As will be appreciated by those skilled in the art, a particular disease or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the compounds of the present invention may be used to treat or prevent any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the compounds of the present invention may be used to treat or prevent any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the compounds of the present invention may be used to lower the chances of having a cardiovascular event (such as a heart attack, myocardial infarction or stroke) in a patient with coronary heart disease.

In certain embodiments, the compounds of the present invention may be used to treat or prevent diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides methods of treating or preventing a neurological disease associated with an abnormal blood brain barrier (BBB) function, inflammation, and/or microglia activation in a subject in need thereof. In some embodiments, the present invention provides methods of treating a neurological disease associated with an abnormal blood brain barrier (BBB) function, inflammation, and/or microglia activation in a subject in need thereof. The methods comprise administering to the subject a therapeutically effective amount of a compound of the present invention. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides methods of treating or preventing disease associated with a subject with blood brain barrier (BBB) leakage. In some embodiment, the present invention provides methods of treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the compounds of the present invention may be used to treat a neurodegeneration disease in a subject. In one embodiment, the compounds of the present invention may be used to prevent a neurodegeneration disease in a subject. The methods comprise administering to a subject in need thereof a compound of the invention, e.g., as a pharmaceutical composition comprising a compound of the invention. In one embodiment, the compounds of the present invention may be used to treat a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier. In one embodiment, the subject which is administered an agent that inhibits the activity of Lp-PLA$_2$ is a human.

In one embodiment, the present invention provides methods of treating or preventing a subject with or at risk of vascular dementia. The methods comprise administering to the subject a compound of the invention, e.g., as a pharmaceutical composition comprising a therapeutically effective amount of a compound of the present invention. In one embodiment, the present invention provides methods of treating a subject with or at risk of vascular dementia. In a certain embodiment, the vascular dementia is associated with Alzheimer's disease.

In certain embodiments, the present invention provides methods of decreasing beta amyloid, referred to as "Aβ" accumulation in the brain of a subject. The methods comprise administering to a subject in need thereof a pharmaceutical composition comprising a therapeutically effective amount of a compound of the present invention. In a further embodiment, the beta amyloid is Abeta-42.

In certain embodiments, when a subject is administered a therapeutically effective amount of a compound of the present invention, the methods may further comprise administering to the subject another therapeutic agent that may be useful in treating the neurodegenerative disease for which the subject is being treated, or that may be a co-morbidity. In one embodiment, the present invention provides methods of slowing or delaying the progression of cognitive and function decline in patients with mild Alzheimer's disease. In certain embodiment, the compounds of the present invention described herein may be used as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides methods of slowing or delaying the progression of cognitive or function decline in a patient with mild or moderate Alzheimer's disease and/or cerebrovascular disease (CVD) comprise administering a therapeutically effective amount of a compound of the present invention to the patient who has been administered an agent used to provide symptomatic treatment to Alzheimer's disease (e.g., ARICEPT® or memantine) for 6 months or longer.

In certain embodiments, the present invention relates to methods of treating or preventing metabolic bone diseases by administering to the subject in need thereof a therapeutically effective amount of a compound of the present invention. In some embodiments, the present invention relates to methods of treating metabolic bone diseases by administering to the subject in need thereof a therapeutically effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diabetes, metabolic syndrome, insulin resistance, hyperparathyroidism and related diseases. In a further embodiment, the subject in need thereof is a human.

It is believed that methods of preventing osteoporosis and/ or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In a further embodiment, methods for inhibiting Lp-PLA$_2$ by reducing and/or down-regulating the expression of Lp-PLA$_2$ RNA are provided. In a further embodiment, preventing and/or reducing loss of bone mass and/or loss of bone density leads to preventing or reducing symptoms associated with metabolic bone diseases such as osteoporosis and/or osteopenic diseases.

In certain embodiments, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides methods for treating and/or preventing ocular diseases by administering a therapeutically effective amount of a compound of the present invention. In some embodiments, the present invention provides methods for treating ocular diseases by administering a therapeutically effective amount of a compound of the present invention. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. Further, in one embodiment, the present invention relates to methods for treating ocular diseases by administering a compound of the present invention to inhibit Lp-PLA$_2$. Exemplary ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide methods for treating or preventing diabetic macular edema in a subject. In some embodiments, the present invention provides methods for treating diabetic macular edema in a subject. The method comprises administering to a subject in need thereof a therapeutically effective amount of a compound of the present invention.

In certain embodiments, the present invention provides methods of treating or preventing a subject with or at risk of macular edema. In some embodiments, the present invention provides methods of treating a subject with or at risk of macular edema. The methods comprise administering to the subject a therapeutically effective amount of a compound of the present invention. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides methods of treating or preventing glaucoma or macular degeneration. In some embodiments, the present invention provides methods of treating glaucoma or macular degeneration. The methods comprise administering to the subject a therapeutically effective amount of a compound of the present invention.

In one embodiment, the present invention provides methods of treating or preventing a disease associated with the breakdown of the inner blood-retinal barrier in a subject in need thereof.

In one embodiment, the present invention provides methods of treating a disease associated with the breakdown of the inner blood-retinal barrier in a subject in need thereof. The methods comprise administering to the subject a therapeutically effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating or preventing posterior uveitis or any of these systemic inflammatory diseases by administering a therapeutically effective amount of a compound of the present invention. In one embodiment, the present invention provides methods for treating posterior uveitis or any of these systemic inflammatory diseases by administering a therapeutically effective amount of a compound of the present invention.

It is believed that Lp-PLA$_2$ inhibitors may have beneficial effects on diseases associated with M1/M2 macrophage polarization. The belief is based on the following studies. A study was carried out by GSK to investigate the relationship between M1/M2 macrophage polarization and different diseases. 94 human markers described in Martinez F O et al., which distinguished M1 and M2 phenotypes was used against a GSK subscribed GeneLogic database. (See Martinez F O et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, and aortic aneurysm have M1/M2 imbalance.

A further study was carried out to study the impact of Lp-PLA$_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-((9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597). In this preventive treatment model, the compound was administered at day 0 (day of immunization) and continued to administer until day 22. The study lasted for 25 days. Rats were subsequently monitored for symptoms of EAE. Rats were immunized with MBP to develop EAE and symptoms were monitored daily. Plasma Lp-PLA$_2$ activity, OxLDL, and LysoPC concentration were determined at different time points through the course of EAE. The results showed that plasma Lp-PLA$_2$ activity, OxLDL, and LysoPC concentrations increased as the clinical EAE disease progressed in the model, which indicates that they played a role in the pathology development. Lp-PLA$_2$ inhibitor treatment led to reduction in clinical disease associated with decreased Lp-PLA$_2$ activity and LysoPC levels in rat EAE plasma. Hence, inhibition of Lp-PLA$_2$ activity is beneficial in ameliorating disease in the rat EAE model.

Ex vivo analysis of proinflammatory (M1) and anti-inflammatory (M2) markers in control and compound treated EAE rats. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in certain embodiments, the present invention provides methods of treating or preventing disease associated with macrophage polarization, for example, M1/M2 macrophage polarization. In some embodiments, the present invention provides methods of treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS) and other autoimmune diseases that are associated with macrophage polarization.

Treatment and or prevention of a disease associated with Lp-PLA$_2$ activity may be achieved using a compound of this invention as a monotherapy, or in dual or multiple combination therapy. For example, the compounds of the present invention may be used to treat or prevent the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312. In one embodiment, the compounds of the present invention may be used with one or more statins. The statins are a well-known class of cholesterol lowering agents and include atorvastatin, simvarstatin, pravastatin, cerivastatin, fluvastatin, lovastatin and rosuvastatin. In a certain embodiment, the compounds of the present invention may be used with an anti-diabetic agent or an insulin sensitizer. In one embodiment, a compound of the present invention may be used with PPAR gamma activators, for instance GI262570 (GlaxoSmithKline) and the glitazone class of compounds such as rosiglitazone, troglitazone and pioglitazone. Such agents may be administered in therapeutically effective amounts, e.g., as is known in the art, or lesser or greater amounts than known in the art provided that the amount administered is therapeutically effective.

Combination therapy includes administration of the therapeutic agents in separate dosage forms or together in a single dosage form. Combination therapy may involve simultaneous administration or separate administration of the therapeutic agents, which may be substantially simultaneous or substantially separate administration. Typically, combination therapy will involve administration of each agent such that therapeutically effective amounts of each agent are present in the subject's body in at least an overlapping period.

One aspect of the present invention provides the use of a compound of the present invention for the preparation of a medicament for carrying out a method described herein. Another aspect of the present invention provides a compound of the present invention for use in carrying out methods of treatment or prevention described herein. A further aspect of the present invention provides a compound described herein or a pharmaceutically acceptable salt thereof, for use in therapy.

F. Composition

The compounds of the present invention may be formulated into pharmaceutical compositions prior to administration to a subject. Accordingly, one aspect of the invention is directed to pharmaceutical compositions comprising a compound of the invention and one or more pharmaceutically-acceptable excipients. In accordance with another aspect of the invention, a process is provided for the preparation of a pharmaceutical composition including admixing a compound of the Formula (I) or salts thereof, solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the condition being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of the disease described herein will generally be in the range of 0.1 to 100 mg/kg body weight of recipient per day and more usually in the range of 1 to 10 mg/kg body weight per day. Thus, for example, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. It is envisaged that similar dosages would be appropriate for treatment of the other conditions referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, *acacia*, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds of Formula (I) described herein or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof.

What is claimed is:

1. A compound of Formula (I) or a pharmaceutically acceptable salt thereof,

Formula (I)

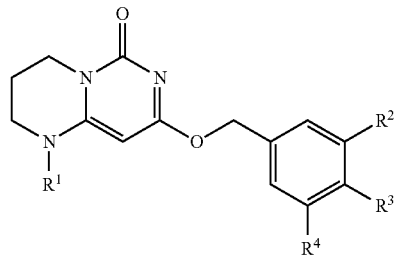

wherein:
- R¹ is selected from the group consisting of cyclopropyl, —CH₂—Ar and CH₂—(C=O)—N(Ra)(Rb), wherein
  Ar is phenyl, optionally substituted with one or more substituents independently selected from the group consisting of halo, OCH₃, and CH₃, and
  Ra and Rb are each independently H or C₁₋₃alkyl, or Ra, Rb, together with the nitrogen atom to which they are attached, join together to form a nitrogen containing heterocyclic ring selected from the group consisting of pyrrolidinyl, morpholinyl, piperazinyl and piperidinyl, wherein the nitrogen containing heterocyclic ring is optionally substituted with one or more substituents independently selected from the group consisting of C₁₋₃alkyl and halo;
- R² is F or H,
- R³ is F or —O—Ar', wherein Ar' is phenyl substituted with one or more substituents independently selected from the group consisting of halo and CF₃, and
- R⁴ is selected from the group consisting of H, F and CN.

2. The compound of Formula (I) or a pharmaceutically acceptable salt thereof according to claim 1, wherein R¹ is —CH₂—(C=O)—N(Ra)(Rb), wherein Ra, Rb, together with the nitrogen atom to which they are attached, join together to form a nitrogen containing heterocyclic ring selected from the group consisting of morpholinyl, piperazinyl and piperidinyl, wherein the nitrogen containing heterocyclic ring is optionally substituted with one or two substituents independently selected from the group consisting of F and CH₃.

3. The compound of Formula (I) or a pharmaceutically acceptable salt thereof according to claim 1, wherein R² is F.

4. The compound of Formula (I) or a pharmaceutically acceptable salt thereof according to claim 1, wherein R³ is F.

5. The compound of Formula (I) or a pharmaceutically acceptable salt thereof according to claim 1, wherein R⁴ is H or F.

6. The compound of Formula (I) according to claim 1 has the structure of

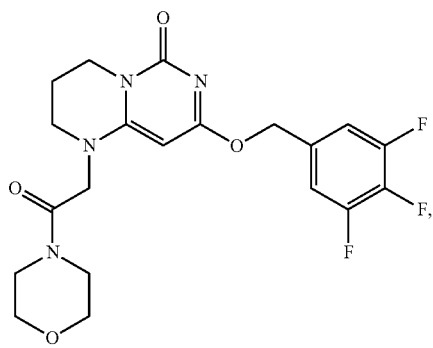

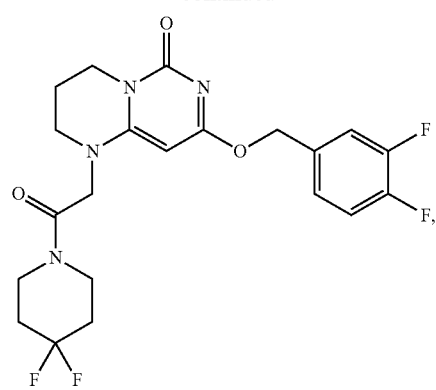

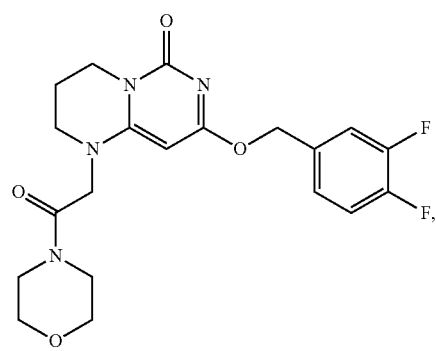

or a pharmaceutically acceptable salt thereof.

7. The compound of Formula (I) or a pharmaceutically acceptable salt thereof according to claim 1, which is selected from the following formula:

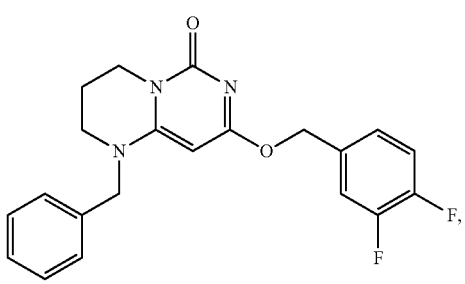

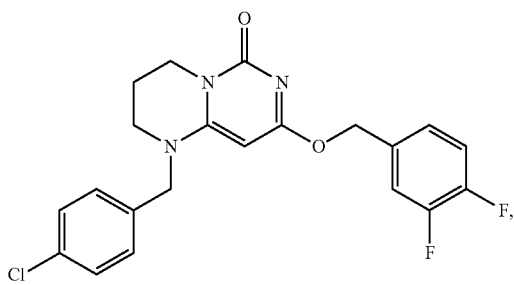

41
-continued
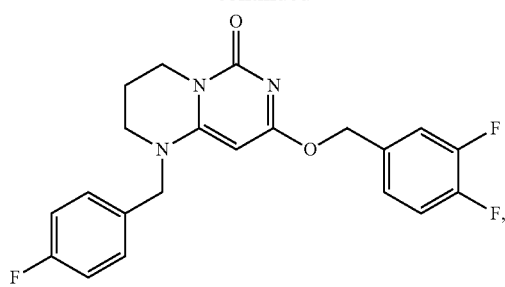
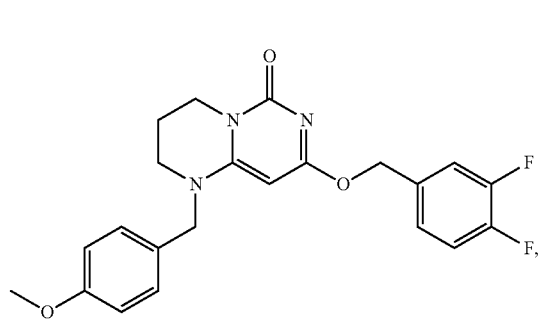
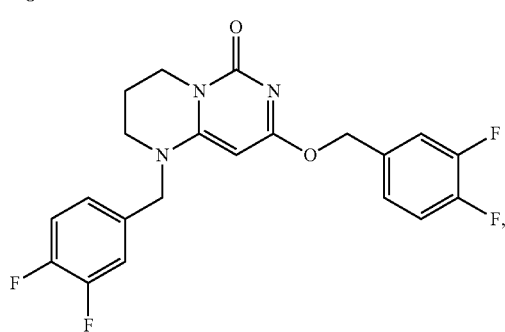
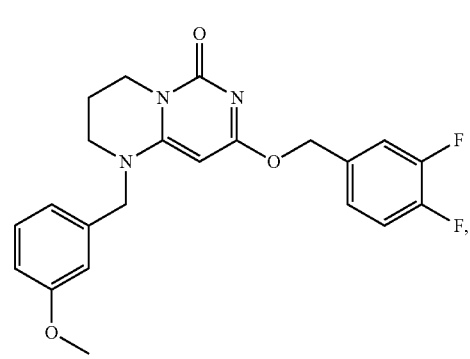
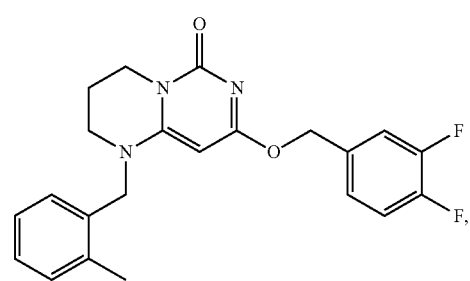
42
-continued
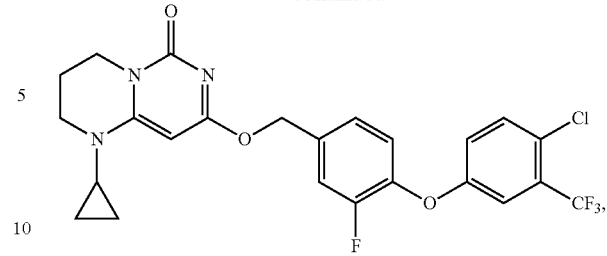
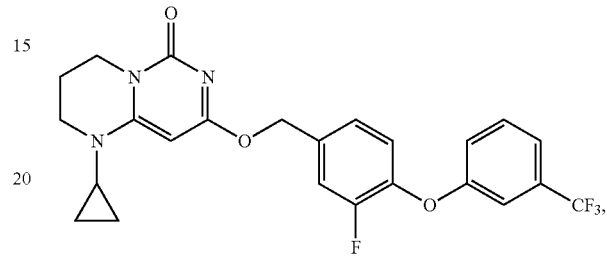
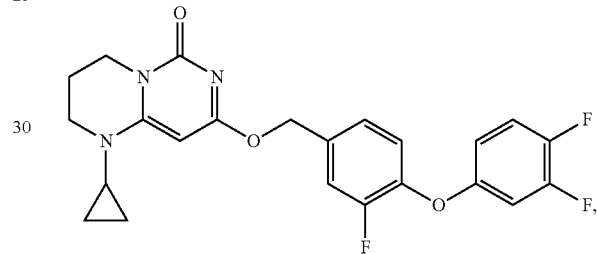
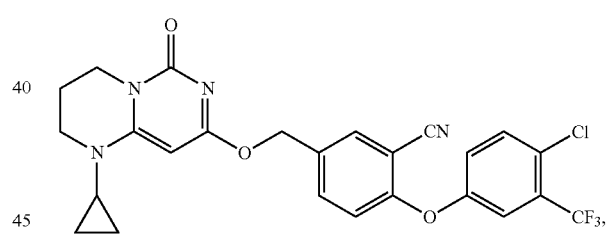
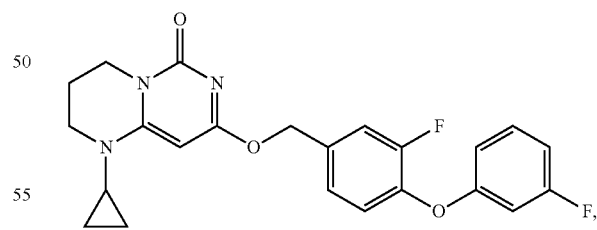
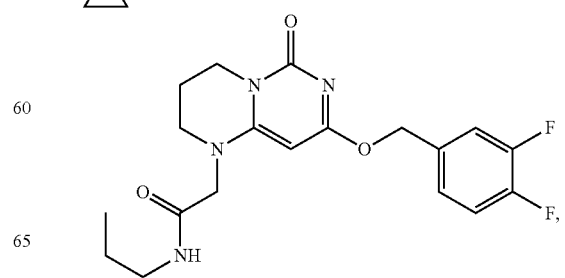

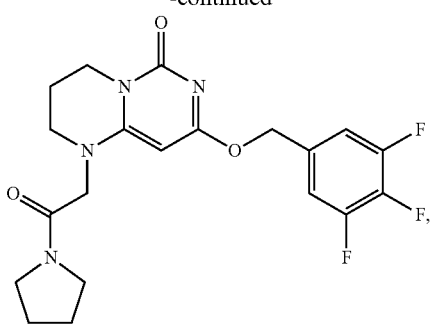
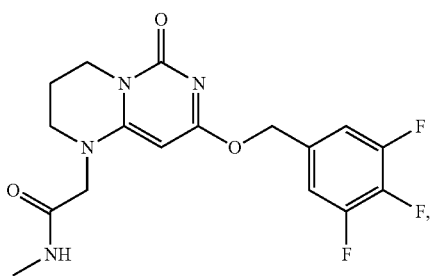
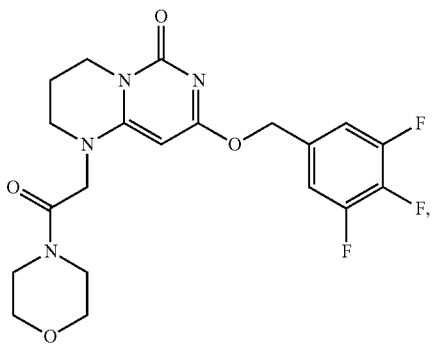
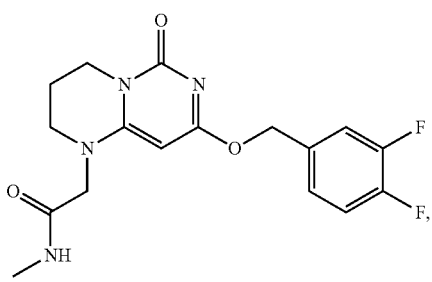
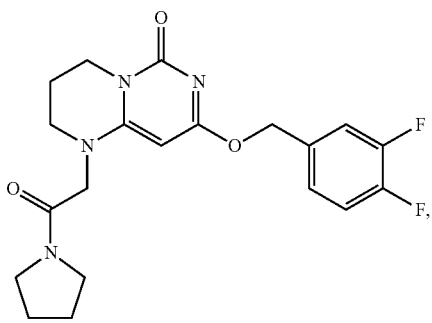
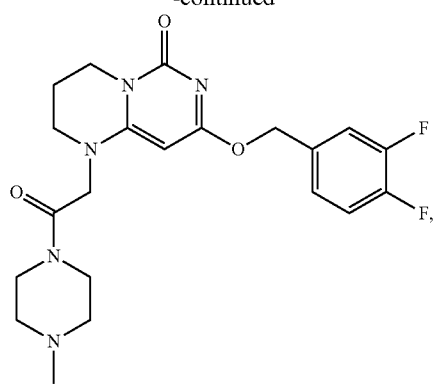
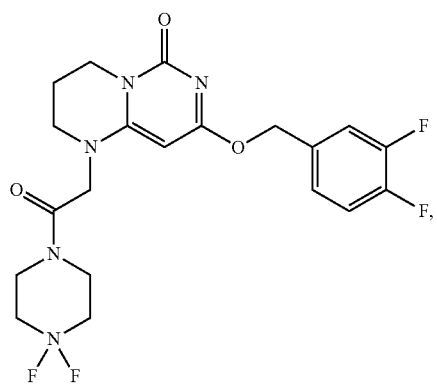
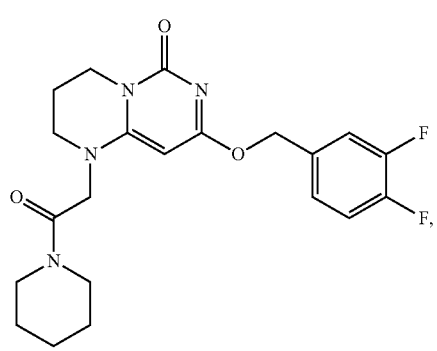
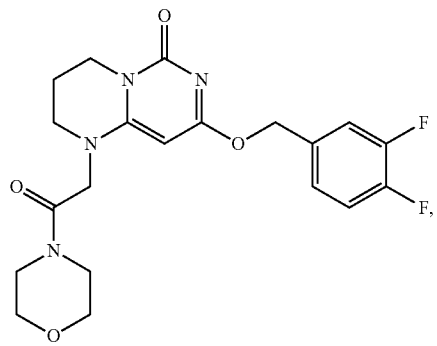

-continued

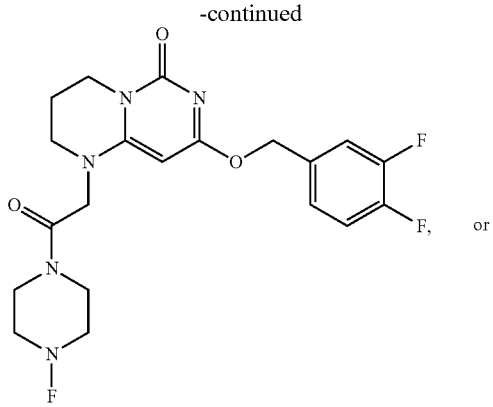

or

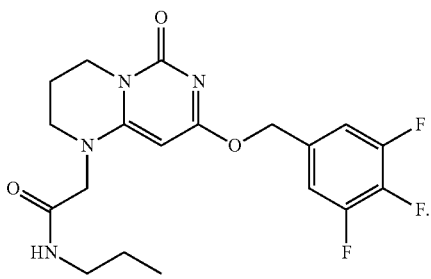 [SMILES: CCCNC(=O)CN1CCCn2c1cc(OCc1cc(F)c(F)c(F)c1)nc2=O]

or a pharmaceutically acceptable salt thereof.

8. A pharmaceutical composition comprising a compound of Formula (I) or a pharmaceutically acceptable salt thereof according to claim 1 and one or more pharmaceutically acceptable excipients.

9. A method for treating neurodegeneration disease mediated by Lp-PLA2 in a subject in need thereof comprising administering to the subject a therapeutically effective amount of a compound of Formula (I), or a pharmaceutically acceptable salt thereof according to claim 1.

10. The method according to claim 9, wherein the neurodegeneration disease is Alzheimer's disease.

11. A method for treating atherosclerosis in a subject in need thereof comprising administering to the subject a therapeutically effective amount of a compound of Formula (I) or a pharmaceutically acceptable salt thereof according to claim 1.

12. The method according to claim 1, wherein the subject is human.

* * * * *